(12) United States Patent
Ernest et al.

(10) Patent No.: US 7,171,699 B2
(45) Date of Patent: *Feb. 6, 2007

(54) DISPOSABLE URINE COLLECTION DEVICE

(76) Inventors: Theresa Ernest, 31360 Wild Oak Hill, Fair Oaks Ranch, TX (US) 78015; Kimberly L. Tomes, 8414 Triple Crown, Fair Oaks Ranch, TX (US) 78015

( * ) Notice: Subject to any disclaimer, the term of this patent is extended or adjusted under 35 U.S.C. 154(b) by 141 days.

This patent is subject to a terminal disclaimer.

(21) Appl. No.: 10/761,813

(22) Filed: Jan. 21, 2004

(65) Prior Publication Data

US 2004/0216220 A1 Nov. 4, 2004

Related U.S. Application Data

(63) Continuation-in-part of application No. 10/302,058, filed on Nov. 22, 2002, now Pat. No. 6,912,737.

(51) Int. Cl.
*A47K 11/00* (2006.01)

(52) U.S. Cl. .................. 4/144.2; 4/144.1; 4/144.3

(58) Field of Classification Search ...... 4/144.1–144.3, 4/222, 233; 604/393, 402
See application file for complete search history.

(56) References Cited

U.S. PATENT DOCUMENTS

| | | | |
|---|---|---|---|
| 4,457,314 A | 7/1984 | Knowles | |
| 4,601,081 A | 7/1986 | Sutton et al. | |
| 4,608,046 A | 8/1986 | Towfigh | |
| 4,645,251 A | 2/1987 | Jacobs | |
| 4,731,065 A * | 3/1988 | Yamada | 604/355 |
| 4,756,029 A | 7/1988 | Zieve et al. | |
| 4,781,713 A | 11/1988 | Welch et al. | |
| 4,857,064 A | 8/1989 | Mendoza | |
| 4,996,727 A | 3/1991 | Wyatt | |
| 5,301,806 A * | 4/1994 | Olson | 206/278 |
| 5,318,549 A | 6/1994 | Yang | |

(Continued)

FOREIGN PATENT DOCUMENTS

EP 0788 327 B1 8/1997

OTHER PUBLICATIONS

RESTOP, Disposable Emergency Toilet Supplies, "Pee Bag", advertisement, (visited Jan. 17, 2003), at http://www.survivalcenter.com/Emergency%20Toilet%20Supplies.html.

(Continued)

*Primary Examiner*—Khoa D. Huynh
(74) *Attorney, Agent, or Firm*—Cox Smith Matthews Incorporated

(57) ABSTRACT

A disposable urine collection device for use by a person which includes an absorbent pad for the collection of urine and a glove attached to the absorbent pad. The glove design includes a mitt for insertion of the user's hand into the device under the absorbent pad through the sleeve of the glove. The absorbent pad is composed of a waterproof plastic liner, a hydrophilic gel and absorbent material layer, and panels of absorbent material. Various embodiments include additional layers in the absorbent pad such as a top protective layer and an absorbent rim. The hand of the user is inserted into the mitt of the glove prior to urination and removed after urination. The sleeve of the glove is inverted over the top of the absorbent pad upon removal from the user's hand. The apparatus may then be secured prior to disposal by various closure means.

9 Claims, 12 Drawing Sheets

U.S. PATENT DOCUMENTS

| | | | |
|---|---|---|---|
| 5,354,132 A | 10/1994 | Young et al. |
| 5,370,637 A | 12/1994 | Brodeur |
| 5,404,999 A | 4/1995 | Bednar |
| 5,438,708 A | 8/1995 | Jacovitz |
| 5,473,789 A | 12/1995 | Oster |
| 5,662,630 A | 9/1997 | Raynie |
| 5,678,564 A | 10/1997 | Lawrence et al. |
| 5,740,554 A | 4/1998 | Reed |
| 5,885,262 A | 3/1999 | Wheeler |
| 5,885,265 A | 3/1999 | Osborn, III et al. |
| 5,895,349 A | 4/1999 | Tihon |
| 5,966,748 A | 10/1999 | Young et al. |
| 5,991,932 A | 11/1999 | Wagner |
| 6,025,535 A | 2/2000 | Octavio et al. |
| 6,183,454 B1 | 2/2001 | Levine et al. |
| 6,186,990 B1 | 2/2001 | Chen et al. |
| 6,202,224 B1 | 3/2001 | Freeman |
| 6,222,091 B1 | 4/2001 | Beihoffer et al. |
| 6,258,997 B1 | 7/2001 | Johansson et al. |
| 6,434,757 B1 | 8/2002 | Filsouf |
| 6,514,602 B1 | 2/2003 | Zhao et al. |

OTHER PUBLICATIONS

Travel-John™ Disposable Urination Pouch, advertisement, (visited Jan. 17, 2003), at http://www.safetycentral.com/travdisurpou.html.

Rolling I Innovations, The Spare BLADDER™, advertisement, (visited Jan. 17, 2003), at http://www.sparebladder.com.

Stella, Women: No Toilet? No Problem!, http://www.alpharubicon.com/med/womengottago.htm, Nov. 26, 2005 (2 sheets).

Anonymous female aviator, "To Pee or Not to Pee," http://www.safetycenter.navy.mil/media/approach/issues/mar03/ToPeeorNot.htm, date unknown (2 sheets).

Hit P-mate Device Coming to the United States—Allowing Women Worldwide to Pee Standing Up!, http://www.send2press.com/newswire/print/news, Oct. 17, 2005 (2 sheets).

Petz Scholtus, "Peeing in your pants—the ideal public toilet accessory for women," www.treehugger.com/files/2005/09/peeing_in_your.php, Sep. 26, 2005 (4 sheets).

Festival Network Online, "Magic Cone," http://magic-cone.com, Printed Apr. 5, 2006 (2 sheets).

"P-Mate USA—How to use the P-Mate," http://www.pmateusa.com/how.php, Printed Apr. 5, 2006 (1 sheet).

"Travel John" Personal Urination Pouch, http://www.acespilotshop.com/pilot-supplies/safety/travel-john.htm, Printed Apr. 5, 2006 (1 sheet).

"Portable Urinals—Lady J Adapter, " http://www.aircraftspruce.com/catalog/pspages/liljohn2.php, Printed Apr. 5, 2006 (1 sheet).

* cited by examiner

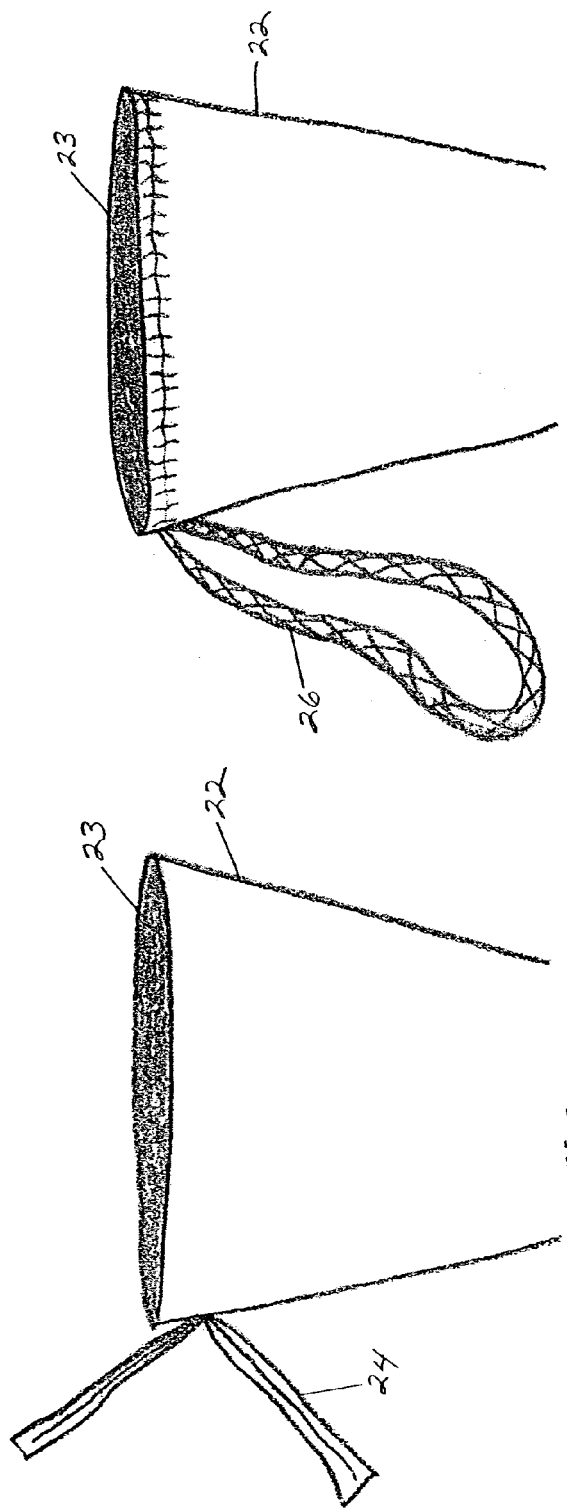
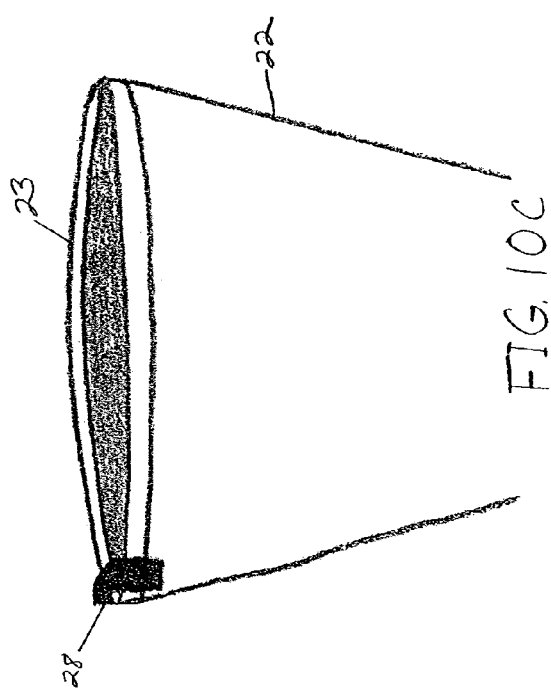

DISPOSABLE URINE COLLECTION DEVICE

RELATED APPLICATIONS

This is a Continuation-in-Part of U.S. application Ser. No. 10/302,058 filed Nov. 22, 2002, now U.S. Pat. No. 6,912,737.

FIELD OF THE INVENTION

The present invention relates generally to portable urinary devices. The present invention relates more specifically to a self-contained disposable urine collection device which allows comfortable and hygienic urination.

DESCRIPTION OF THE RELATED ART

In our highly mobile society, people sometimes face a unique dilemma regarding the issue of where to urinate, especially while traveling in a car. For example, individuals caught in traffic jams or snowstorms have limited options available for solving such a problem. Particularly in remote areas, public restrooms are often unavailable. Finding a secluded spot to urinate outdoors is often impossible. Even if such a place is located, the process is often uncomfortable, especially for women. For elderly or handicapped individuals, limited mobility may eliminate outdoor urination as an option.

Even if a restroom is available while traveling, people are often reluctant to use it because of concerns regarding sanitation. Growing fears of infection with the AIDS virus, Herpes, and many other microorganisms has made people more reluctant to expose themselves to unnecessary health risks. Many people are concerned about potential health hazards due to transmission of diseases from use of a public restroom. Although it is debatable as to whether these organisms remain infectious in such an environment, many individuals would prefer not to take this risk.

Moreover, when traveling in remote areas, using a public facility may involve a substantial safety risk for personal assault. This is particularly true for travel at night, especially for women and elderly individuals.

The alternative of holding the urine for extended periods of time while waiting to arrive at a suitable destination presents other undesirable problems. Apart from the obviously painful nature of such an option, the practice of delaying urination can result in medical problems for certain individuals who are at risk for bladder and kidney infections. For people who suffer from urinary urgency, loss of sphincter control, and various other conditions, waiting to urinate may not be possible.

Another important use of a portable disposable urinary device is in medical settings, such as hospitals, nursing homes, and rehabilitation centers. Avoiding catheterization is preferable whenever possible. However, patients are often unable or reluctant to make a painful trip to the restroom or use a bedpan or urinal due to discomfort or weakness from a surgery or illness, or due to mobility constraints such as a wheelchair. Moreover, nursing home residents frequently do not want to wear disposable diaper products all day because of chaffing, odor, dignity, and discomfort.

Obviously, this problem is not new, and various attempts have been made to provide urination alternatives. None of these devices, however, have solved the problem of providing a portable, disposable, and hygienic urinary device that is easy to carry and use and inexpensive to manufacture.

Efforts to develop urinary devices have led to various designs as exemplified in the following patent disclosures.

U.S. Pat. No. 4,457,314 issued on Jul. 3, 1984 to Knowles claims a female urine collection device and method which includes a cup-shaped receiving chamber with a flexible lip which seals around the urethral orifice. A duct section leads to flexible tubing leading to a compressible collection reservoir. The chamber and reservoir are mounted in a housing of soft absorbent material.

U.S. Pat. No. 5,678,564 issued on Oct. 21, 1997 to Lawrence et al. describes a liquid removal system which utilizes a membranous interface device which maintains a vacuum on one side. The vacuum operates such that liquid passes through the membrane and is removed to a receptacle for disposal.

U.S. Pat. No. 4,756,029 issued on Jul. 12, 1988 to Zieve et al. describes a feminine urinary device which permits urinating in a standing position. The device has a hingedly attached flap with expandable walls which permit the side walls to expand downward in order to collect the urine. The pad is held in place against the body for the passage of urine into the expandable receptacle. Alternatively, the device can be designed to include an aperture which attaches to a spout which acts as a conduit for the urine.

U.S. Pat. No. 4,781,713 issued on Nov. 1, 1988 to Welch et al. describes a disposable incontinency pad for females which includes an absorbent pad encased in a moisture resistant layer to prevent leakage. The device includes an ovoid opening with a contoured rim portion which conforms to the urinary area of the wearer. The rim directs urine into the pad and away from the user.

None of the inventions described above provide an easy to use, comfortable, disposable urinary device. Most of these designs present contact surfaces which are uncomfortable and ill-fitting. Some of these devices are also unwieldy to maneuver, especially for discrete disposable use in those areas where the necessity to use such a device is most likely to occur.

SUMMARY OF THE INVENTION

Therefore, the primary object of the present invention, is a comfortable, hygienic urinary device which allows a person to urinate in a variety of positions without wetting clothing and body parts. Another object of the present invention is to provide a device which is convenient to carry, easy to use, and inexpensive to manufacture. Another object of the present invention is to provide a urinary device which is disposable and biodegradable. The present invention would provide a disposable urinary device which could be used in a variety of travel settings. Yet another object of this invention is a disposable urinary device for use in a medical or extended care setting, which could be administered by the patient or resident as well as by the attending nurse or caregiver.

The urinary device of the present invention is a self-contained disposable apparatus with an absorbent concave pad for the collection of urine. The design includes a glove which is attached to the absorbent pad which has a mitt for the user's hand to support the absorbent pad. The absorbent pad is composed of a waterproof liner, absorptive layers, and a protective moisture layer. This device can be used in a variety of positions, such as lying down on the side or back, sitting, or standing. The hand of the user is inserted into the mitt prior to urination and removed after urination by folding the sleeve of the glove over the top of the absorbent pad. The device may then be secured prior to disposal by a variety of methods, including a zipper top closure, twist tie, or drawstring feature, connected to the distal end of the sleeve.

The device includes an absorbent pad which contains several layers. The waterproof plastic liner on the bottom of the pad serves to contain the urine without leakage. The next layer is made of hydrophilic gel and absorbent materials. Next, there are panels of absorbent material to direct and absorb the liquid. The top protective layer is fluid pervious to permit the entrance of urine into the absorptive layers. The rim of the absorbent pad forms a lip which is not only absorbent, but which provides a supportive contour to the device and a soft body-conforming surface to prevent leakage. The absorbent material on the top surface of the device may also be used to wipe away residual urine. An alternative embodiment of the device may also have a separate wipe which is included to wipe away residual urine.

BRIEF DESCRIPTION OF THE DRAWINGS

FIG. 6B is an illustration of the straight panel embodiment of the present invention.

FIG. 7B is an illustration of the boxed panel embodiment of the present invention.

FIG. 8B is an illustration of the circular panel embodiment of the present invention.

FIG. 9B is an illustration of the honeycombed panel embodiment of the present invention.

FIG. 10A is an illustration of the twist tie closure embodiment of the present invention.

FIG. 10B is an illustration of the drawstring closure embodiment of the present invention.

FIG. 10C is an illustration of the plastic zipper closure embodiment of the present invention.

DESCRIPTION OF THE PREFERRED EMBODIMENTS

Figure 1A:
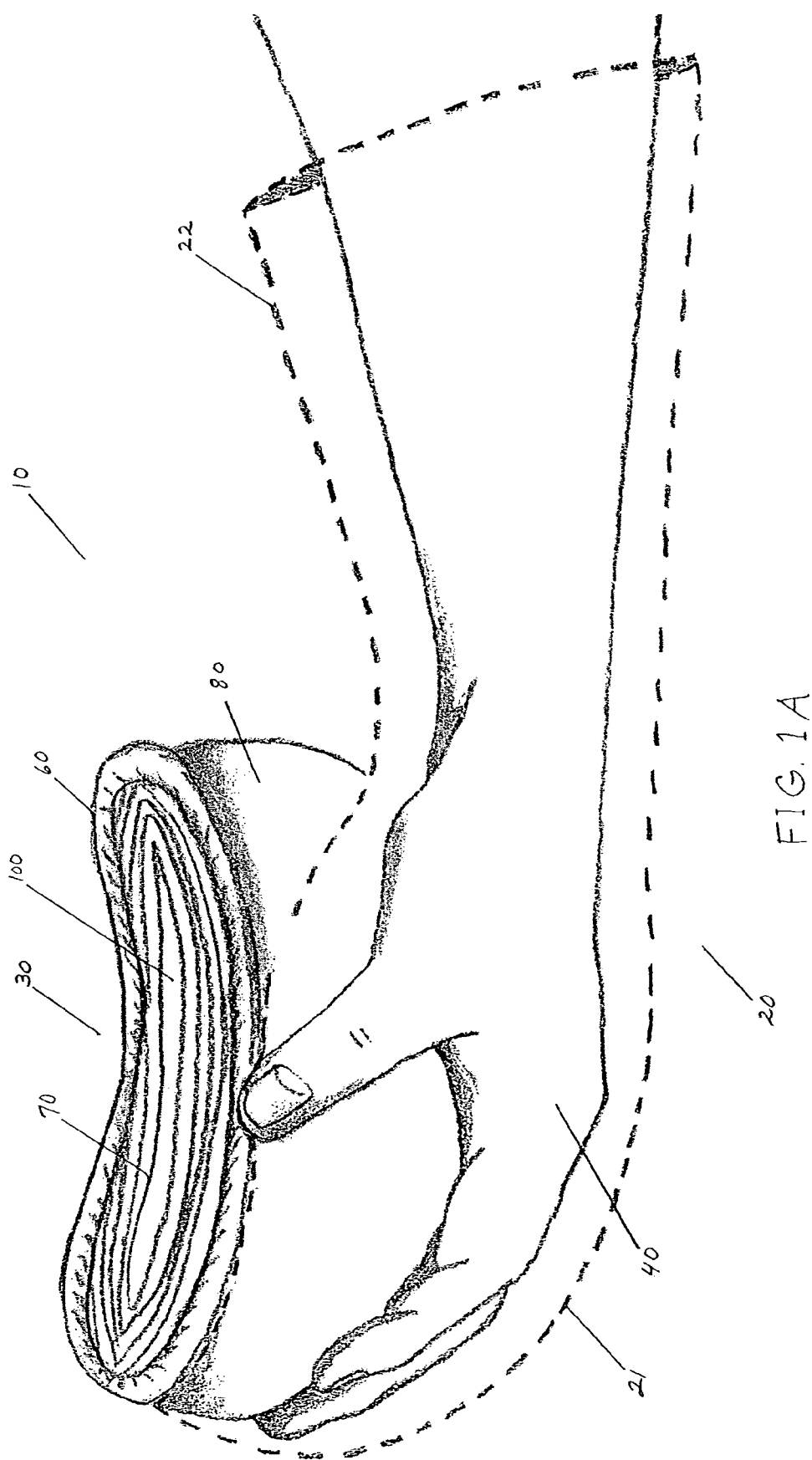
FIG. 1A is a side view of the present invention illustrating the urinary device positioned on the hand of the user.
Figure 1B:
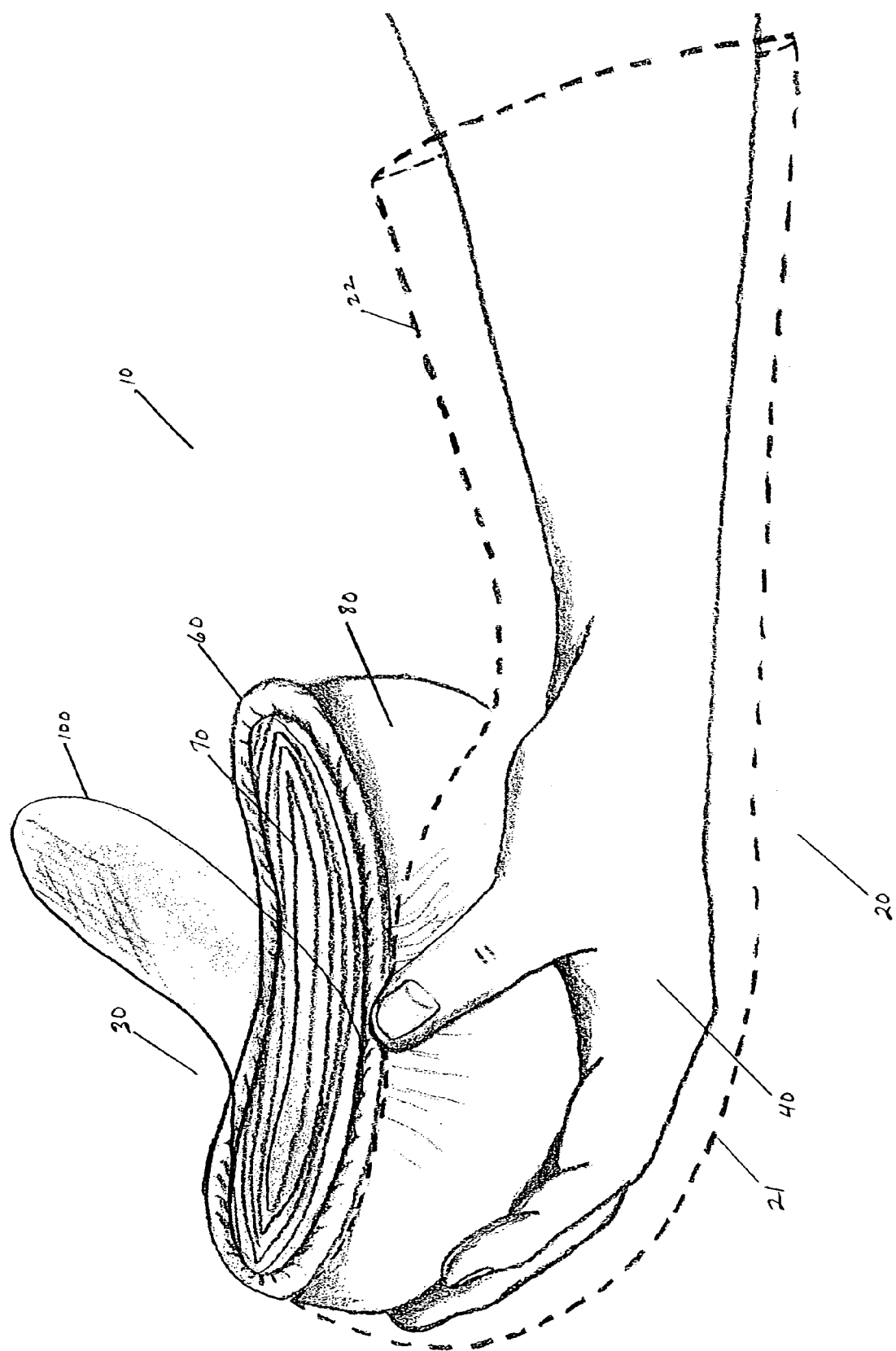
FIG. 1B is a side view of the present invention with the top protective layer of the urinary device lifted away from the rim of the absorbent pad for illustration.
Figure 3:
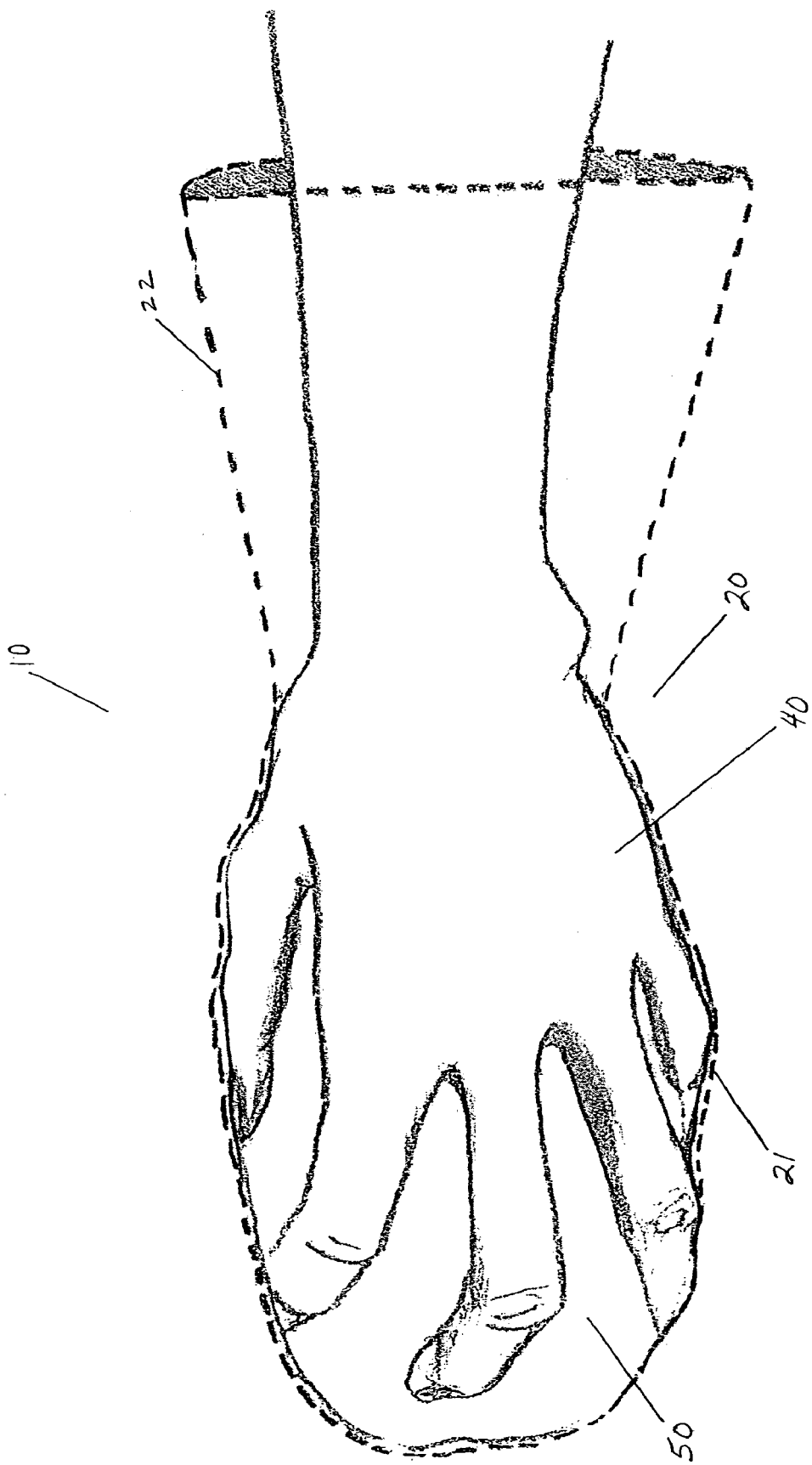
FIG. 3 is a bottom view of the present invention illustrating the urinary device positioned on the hand of the user.

Reference is made first to FIG. 1A for an overview of the urinary device 10 of the present invention. As shown in FIG. 1A, the device is an absorbent pad 30 attached to a waterproof glove 20. The hand 40 of the user is inserted into the sleeve 22 of the waterproof glove 20 such that the hand 40 is in the mitt 21 of the waterproof glove 20 supporting the absorbent pad 30. The absorbent pad 30 has a waterproof lining 80, a rim 60, panels of absorbent material 70, and a top protective layer 100. This top protective layer 100 is shown in a raised position in FIG. 1B to illustrate its attachment to the rim 60 of the absorbent pad 30 as a thin, permeable covering. As shown in FIG. 3, the absorbent pad 30 is preferably preformed such that the shape of the bottom of the pad 50 fits the contour of the hand of the user 40. The rim 60 of the absorbent pad 30 is configured to easily align with the contours of the body, both for comfort and to form a seal when in use.

Figure 2:
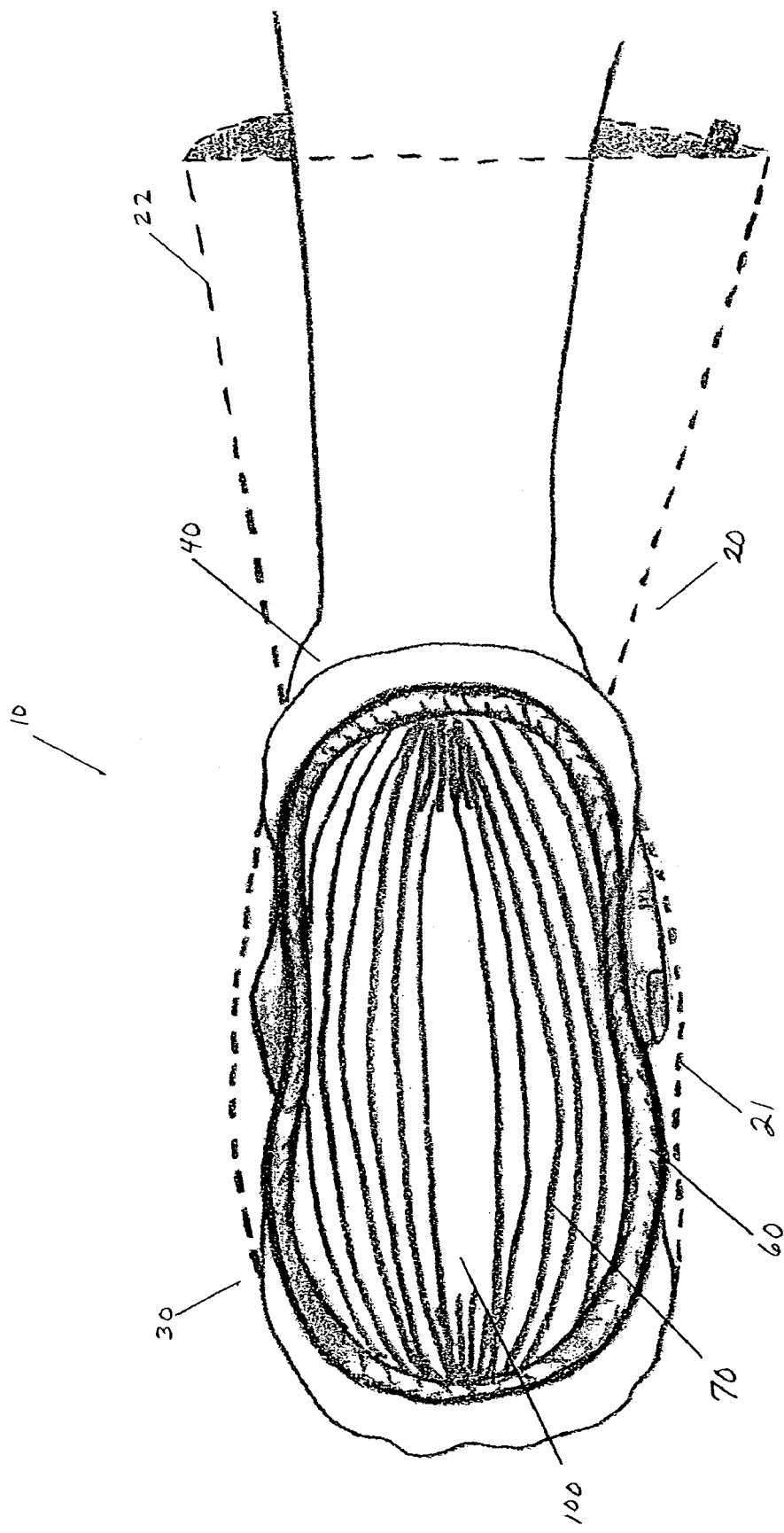
FIG. 2 is a top view of the present invention illustrating the urinary device positioned on the hand of the user.
Figure 4:
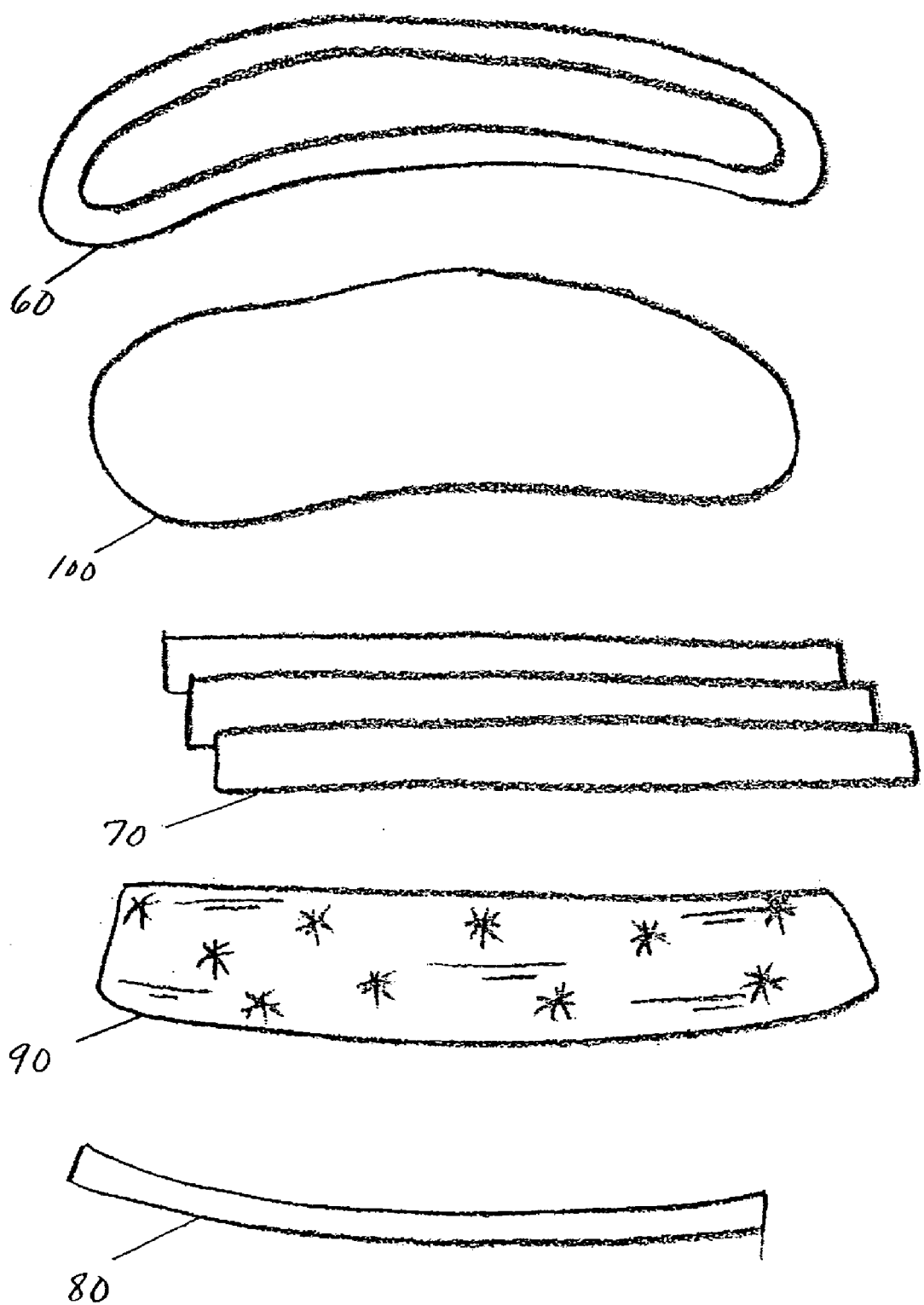
FIG. 4 is an illustration of the layers of the absorbent pad of the present invention.

Continuing, FIG. 2 illustrates the top view of the present invention, showing the panels 70, rim 60, and top protective layer 100 of the preformed absorbent pad 30. As shown in FIG. 4, the absorbent pad 30 is composed of several layers. The bottom layer forms a shell of waterproof lining 80 composed of materials well known in the art such as impervious polyethylene or polypropylene film or thermoplastic polymer to hold the urine within the urinary device 10. The next layer is composed of layers of hydrophilic gel and absorbent materials 90. The hydrophilic gel is made of super-absorbent polymer particles which contain water-absorbing resins that are well known in the art.

Continuing, FIG. 2 illustrates the top view of the present invention, showing the panels 70, rim 60, and top protective layer 100 of the absorbent pad 30. As shown in FIG. 4, the absorbent pad 30 is composed of several layers. The bottom layer forms a shell of waterproof lining 80 composed of materials well known in the art such as impervious polyethylene or polypropylene film or thermoplastic polymer to hold the urine within the urinary device 10. The next layer is composed of layers of hydrophilic gel and absorbent materials 90. The hydrophilic gel is made of super-absorbent polymer particles which contain water-absorbing resins that are well known in the art.

FIG. 4 illustrates the panels 70 which are positioned above the hydrophilic gel and absorbent material layer 90 in the absorbent pad 30. These panels 70 are composed of a non-woven sponge-like material or bonded-fiber fabric layers. In one embodiment, the panels 70 are formed of a non-woven material composed of a cellulose and synthetic fiber blend which is well known in the art. The panels 70 may be configured in various shapes, as is shown in FIGS.

Figure 6A:
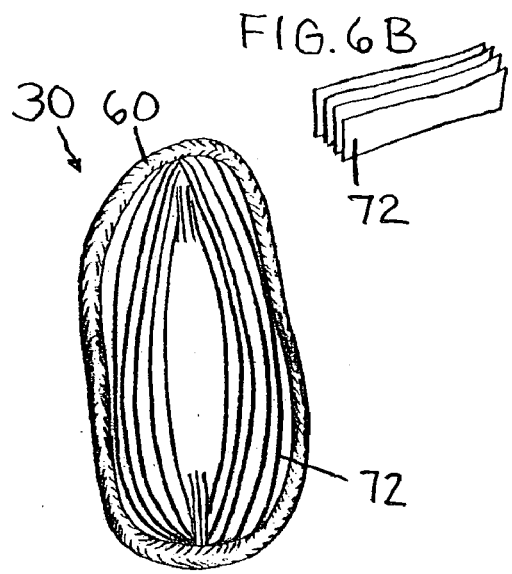
FIG. 6A is a top view illustration of the absorbent pad of the present invention showing the embodiment with a series of straight panels.
Figure 7A:
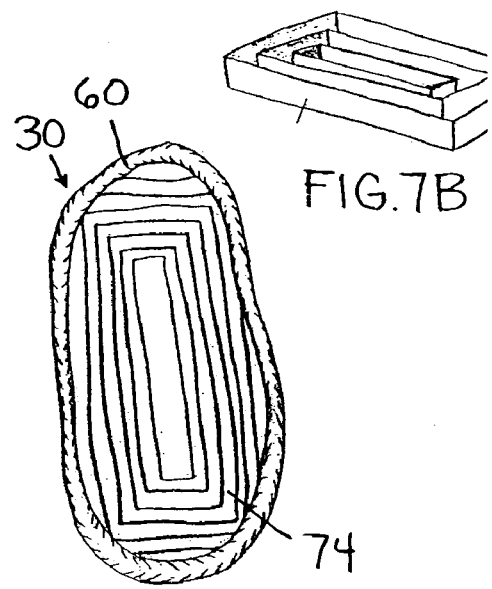
FIG. 7A is a top view illustration of the absorbent pad of the present invention showing the embodiment with a series of boxed panels.
Figure 8A:
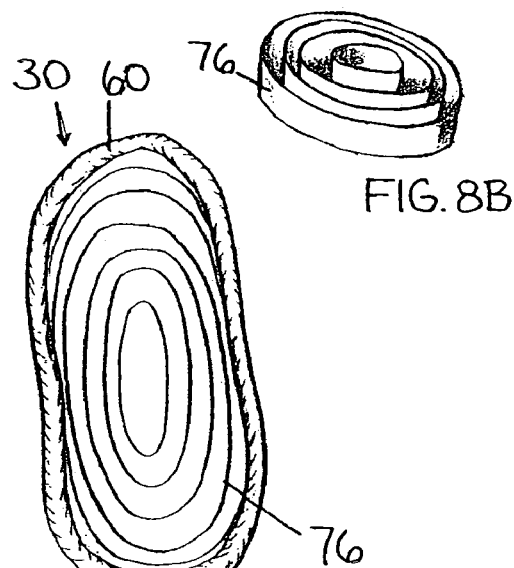
FIG. 8A is a top view illustration of the absorbent pad of the present invention showing the embodiment with a series of circular panels.
Figure 9A:
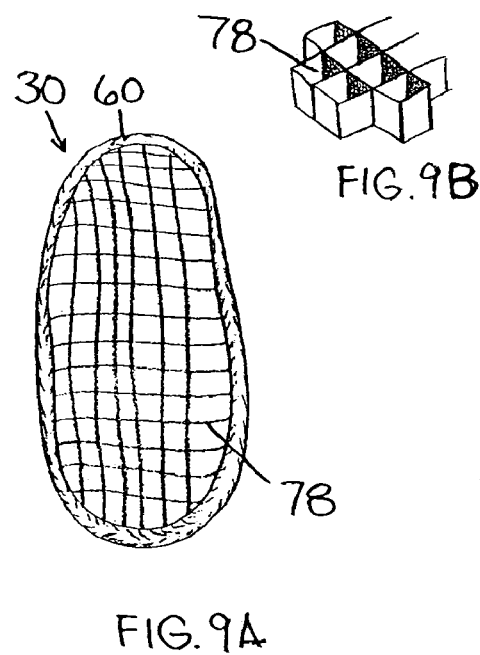
FIG. 9A is a top view illustration of the absorbent pad of the present invention showing the embodiment with a series of honeycombed panels.

6A, 6B, 7A, 7B, 8A, 8B, 9A, and 9B. FIGS. 6A and 6B illustrate the straight configuration 72 of the panels 70 in which they are constructed and arranged lengthwise across the ovoid absorbent pad 30. FIGS. 7A and 7B show the boxed configuration 74 of the panels 70 in which they are rectangularly arranged within the absorbent pad 30. FIGS. 8A and 8B reveal a circular arrangement 76 of the panels 70, in which they are concentrically positioned within the absorbent pad 30. FIGS. 8A and 8B illustrate the honeycombed configuration 78 of the panels 70, in which they are arranged in a lattice type formation within the absorbent pad 30.

Returning to FIG. 4, the next layer in the absorbent pad 30 is the top protective layer 100, which is designed to allow fluids to enter the surface of the absorbent pad 30. This top protective layer is composed of a hydrophilic, fluid pervious, fibrous, non-woven web well known in the art. This layer provides suitable fluid handling capabilities and desirable tactile softness. Other suitable materials known in the art that would also be appropriate include a liquid-pervious cover layer against which individual hydrophobic fibers are arranged. The cover layer contains fiber-free regions to promote liquid transfer through the cover layer. Such an external cover layer is user-friendly as it is both soft and exhibits a dry surface after wetting.

Reference is now made to the rim of the absorbent pad which is illustrated in FIG. 4. The rim forms the lip of the absorbent pad, functioning to shape the pad, prevent leakage, and absorb residual moisture during use. The rim is composed of a soft, absorbent cord constructed from woven fibers.

Figure 5A:
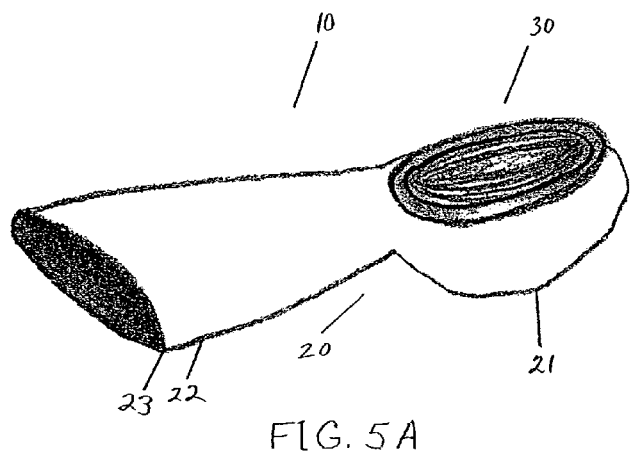
FIG. 5A is an illustration of the urinary device of the present invention.
Figure 5B:
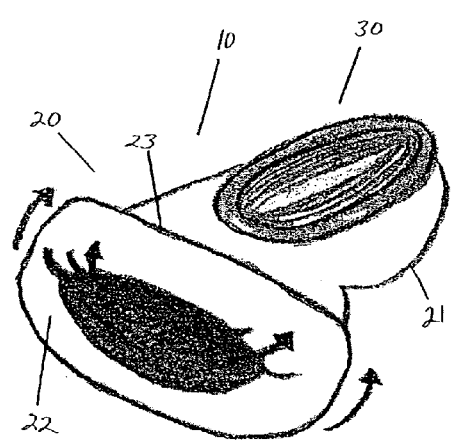
FIG. 5B is an illustration of the urinary device of the present invention showing the glove partially turned inside out.
Figure 5C:
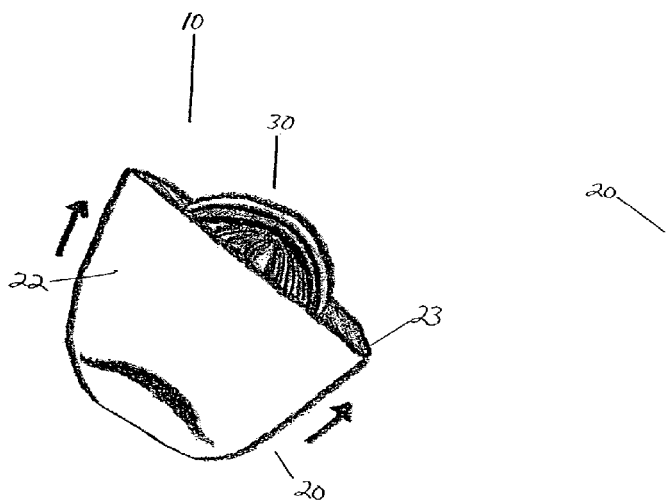
FIG. 5C is an illustration of the urinary device of the present invention showing the glove turned inside out almost completely covering the absorbent pad.

Continuing in FIG. 5A, the urinary device of the present invention is shown after removal from the hand of the user. FIG. 5B illustrates the manner in which the sleeve of the waterproof glove of the urinary device is turned back upon itself as the initial step in covering and disposing of the used article. FIG. 5C shows the urinary device with the absorbent pad almost entirely covered by the inverted sleeve. Finally, in FIG. 5D, the urinary device is illustrated with the absorbent pad completely hidden inside the inverted sleeve. The embodiment of FIG. 5D has a zipper closure feature (also depicted in FIG. 10C) at the distal end of the sleeve for sealing the absorbent pad within the waterproof glove of the urinary device in preparation for disposal.

Alternative closure methods are illustrated in FIGS. 10A and 10B. FIG. 10A shows a twist tie feature located at the distal end of the sleeve of the urinary device. FIG. 10B reveals a drawstring closure design at the distal end of the sleeve of the urinary device.

Figure 11:
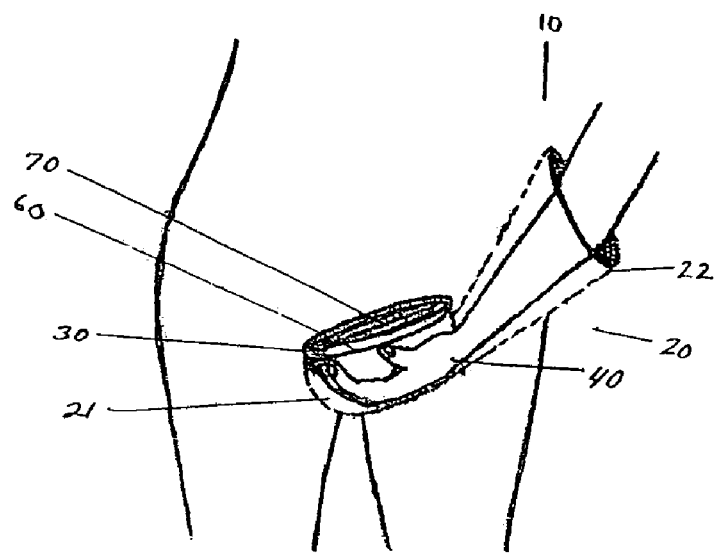
FIG. 11 is an illustration of the absorbent pad of the urinary device of the present invention positioned for use.

Actual use of the urinary device 10 requires inserting the user's hand 40 into the sleeve 22 and mitt 21 of the waterproof glove 20 to cradle the bottom 50 of the absorbent pad 30 (see FIG. 1A). Next, as shown in FIG. 11, the absorbent pad 30 of the urinary device 10 is positioned against the urinary area in such a manner that the user is able to direct the flow of urine into the panels 70 of the absorbent pad 30. After voiding, the user can slide the urinary device 10 forward such that the rim 60 of the absorbent pad 30 absorbs any residual urine present on the body of the user. Alternatively, a disposable wipe may be provided with the device for removal of residual urine.

Figure 12:
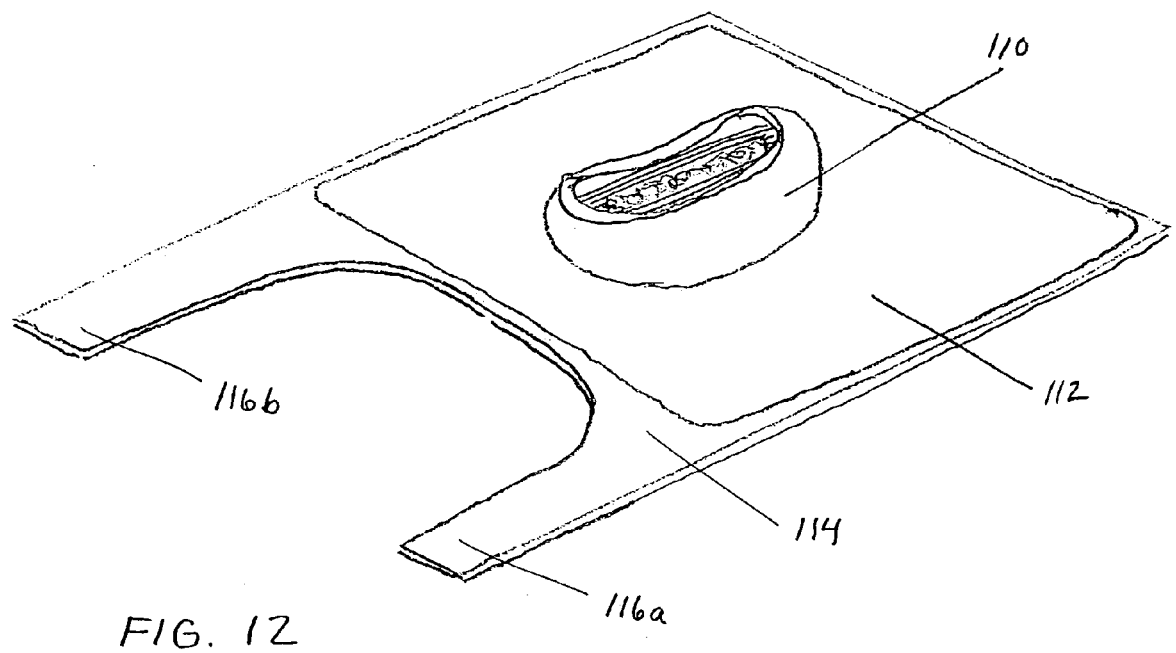
FIG. 12 is a perspective view of an alternate preferred embodiment of the present invention.
Figure 13:
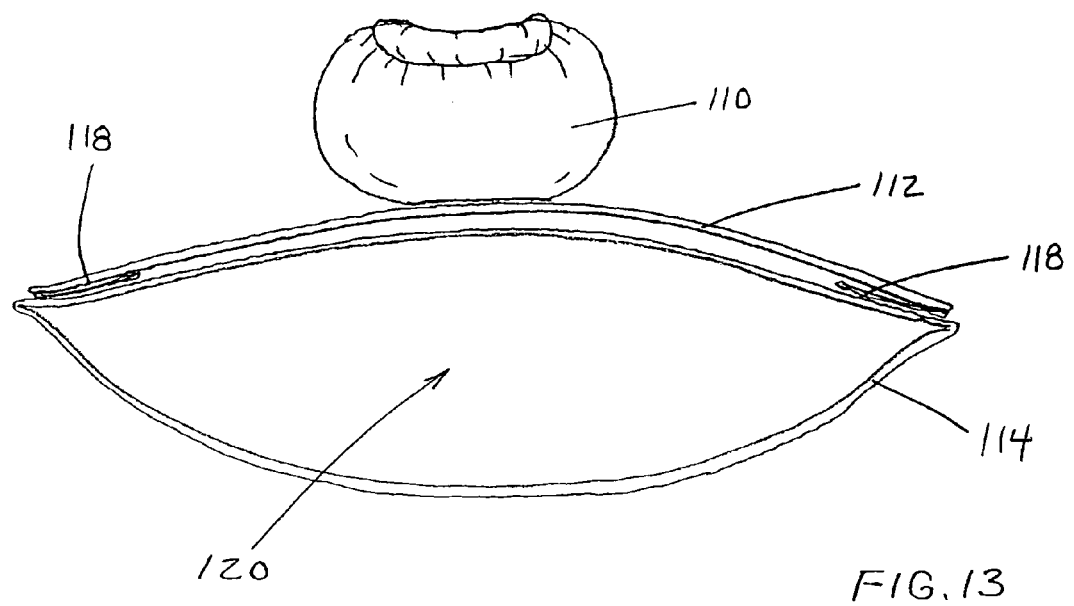
FIG. 13 is a cross sectional view of the alternate preferred embodiment of the present invention shown in FIG. 12.

Reference is now made to FIGS. 12 and 13 for a brief description of an alternate embodiment of the present invention. FIG. 12 is a prospective view of a configuration of the present invention showing urinary device 110 positioned and affixed to a closure sleeve that is easier to manufacture than in the first described embodiment (FIGS. 1A and 1B), but which still maintains most of the functionality required for holding and enclosing the urinary device. As indicated, urinary device 110 is positioned on and adhered to an absorbent sheet 112 that itself is positioned on and adhered to a plastic bag enclosure 114. Bag enclosure 114 may preferably be constructed of a polyethylene material that is light weight, strong, but inexpensive to manufacture. In the present application wherein the enclosure bag 114 serves to hold and eventually enclose urinary device 110 the closure means comprises a pair of bag extensions or "ears" 116A and 116B.

Use of the device shown in FIG. 12 is essentially the same as the use of the first preferred embodiment described above. The user inserts a hand into enclosure bag 114 and holds urinary device 110 through the surface of bag 114 and absorbent pad 112. Absorbent pad 112 serves to provide both comfort to the user and a means for absorbing any leakage or over spill from the urinary device 110.

After use, the user turns the bag enclosure 114 over urinary device 110 and absorbent pad 112 so as to fully enclose them within the waterproof bag. The user then ties together bag extensions 116A and 116B to form a disposable unit.

FIG. 13 shows a side view of the embodiment disclosed and described in FIG. 12. In this view, adhesive material 118 is shown positioned to secure absorbent pad 112 to an upper surface of bag enclosure 114. Bag opening 120 is shown as it would be positioned to receive the user's hand for use of the urinary device 110.

Figure 14:
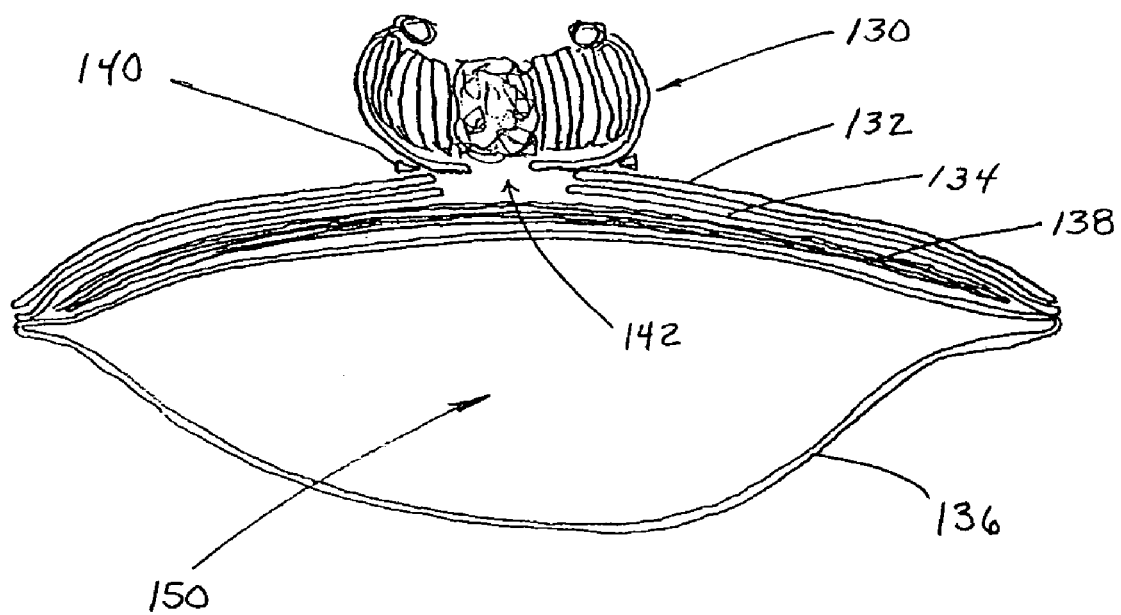
FIG. 14 is a cross sectional view of a further alternate preferred embodiment of the present invention.

Reference is finally made to FIG. 14 for a brief description of a third embodiment of the present invention which comprises a slight modification of the embodiment shown in FIGS. 12 and 13. Instead of being fully enclosed as shown in FIGS. 12 and 13, an alternate configuration of urinary device 130 is shown in cross section. In this view it can be seen that an aperture 142 exists in a lower portion of urinary device 130 beneath the absorbent material therein. Urinary device 130 is, as shown in FIGS. 12 and 13, positioned on and adhered to absorbent pad 132 which itself is positioned on and adhered to a waterproof lining 134. Waterproof lining is itself sealed at its edge to enclosure bag 136. Waterproof lining 134 and absorbent pad 132 also define portals aligned with the portal and the base of urinary device 130. These portals allow excess fluid not absorbed by the absorbent material within urinary device 130 to flow through portal 142 and into a secondary layer of absorbent material 138. All of absorbent material 138 is fully retained between enclosure bag 136 and waterproof lining 134. The only access into this enclosure to absorbent material 138 is through the portals 142 aligned as shown. Use of the embodiment shown in FIG. 14 is the same as that described above with respect to the embodiment disclosed in FIGS. 12 and 13.

Figure 5D:
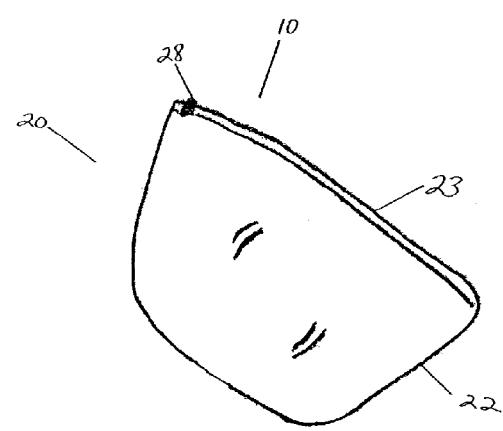
FIG. 5D is an illustration of the urinary device of the present invention showing the glove turned fully inside out around the absorbent pad.

The user then inverts the sleeve 22 of the waterproof glove 20 such that the sleeve 22 completely envelopes the absorbent pad 30 (see FIG. 5D). The user can then seal the closure at the distal end 23 of the sleeve 22 and dispose of the urinary device 10. Alternative embodiments of the urinary device 10 include the absorbent pad 30 without the attached glove 20, either with or without a disposal means, such as a pouch or bag. In an alternative embodiment, the urinary device of the present invention may be manufactured with a deodorizing substance contained within the absorbent pad in order to reduce or eliminate odors. In a medical setting, when fluid intake and output measurement is important, the device may be weighed to determine the quantity of urine excreted, similar to the weighing of diapers in a hospital nursery. The urinary device of the present invention may be designed to accommodate persons of varying size and age. For example, a small device may be most useful for children, providing a better fit and adequate urinary capacity.

Figure 15:
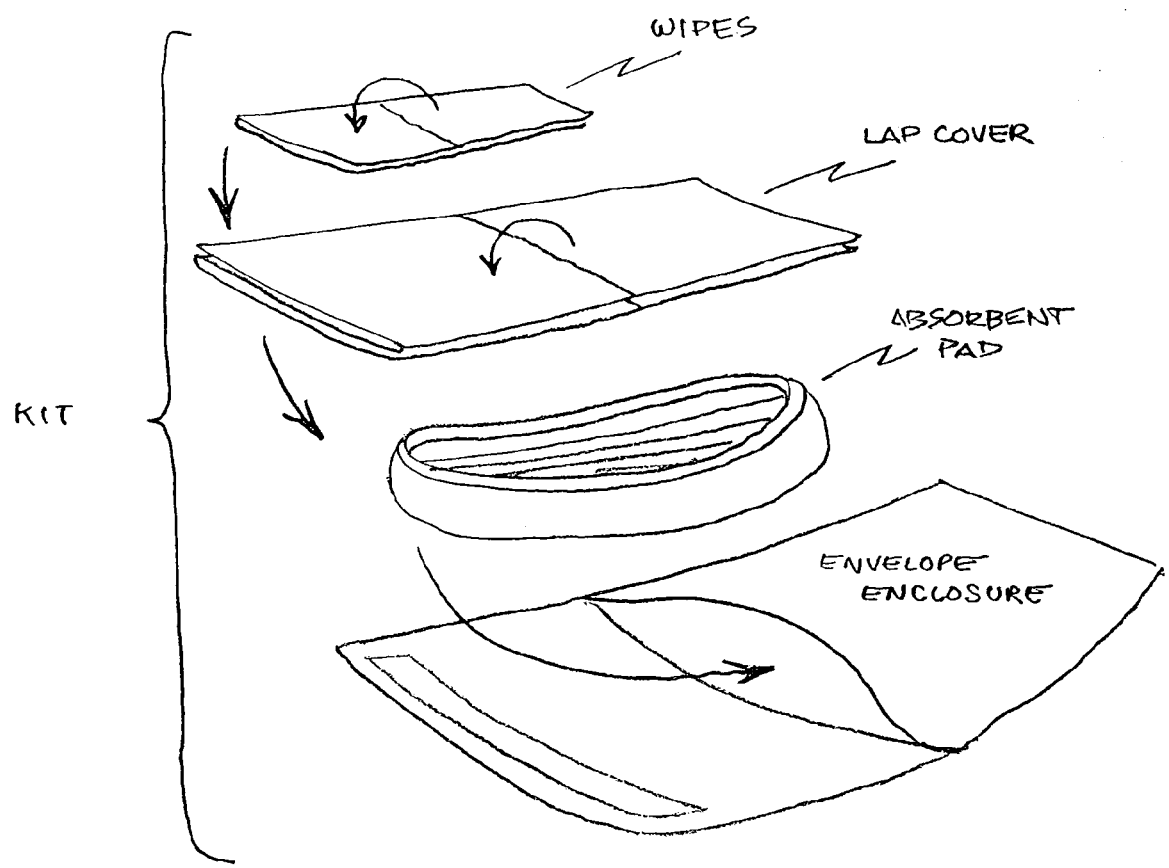
FIG. 15 is an exploded view of the component elements of a kit embodiment of the present invention.

Reference is now made to FIG. 15 for a brief description of the components of a kit that would include the absorbent pad of the present invention. The kit shown is comprised of four main elements that include the absorbent pad, a small wipe pad, a thin lap cover, and the envelope package enclosure. The small wipe pad is provided to the user for cleanliness after use of the product. The wipe pad may be either a soft absorbent material such as a paper tissue or may be a stronger fiber based material that is moistened with antibacterial substances and/or moistening substances. If the wipe is of the moist type, it would be separately enclosed in a thin wrapping to prevent the moisture from escaping into the absorbent pad. If the wipe pad is of the dry type, it could be placed directly on top of the absorbent pad of the present invention within the kit shown in FIG. 15.

The lap cover shown in FIG. 15 is a generally rectangular sheet of paper based material that is folded into a convenient size to be included in the kit. The purpose of the lap cover is to provide some privacy to the user during use of the product in such instances where the location of the use of the product demands if necessary the user of the product may unfold the lap cover and extend it over their abdominal area so as to visually hide their use of the product. It is not anticipated that every situation would demand the use of the lap cover of the kit shown. Single item sales of the product would likely include a lap cover whereas packages that incorporated multiple items of the product may preferably include one lap cover for every three items of the product.

Finally, all three of the packaged components of the kit shown in FIG. 15 would be placed together and inserted into a pliable plastic envelope having a means for sealing the envelope once the kit product components are included inside. The pliable plastic could be heat sealed or may retain an adhesive seal in a manner that is well known in the art.

Figure 16:
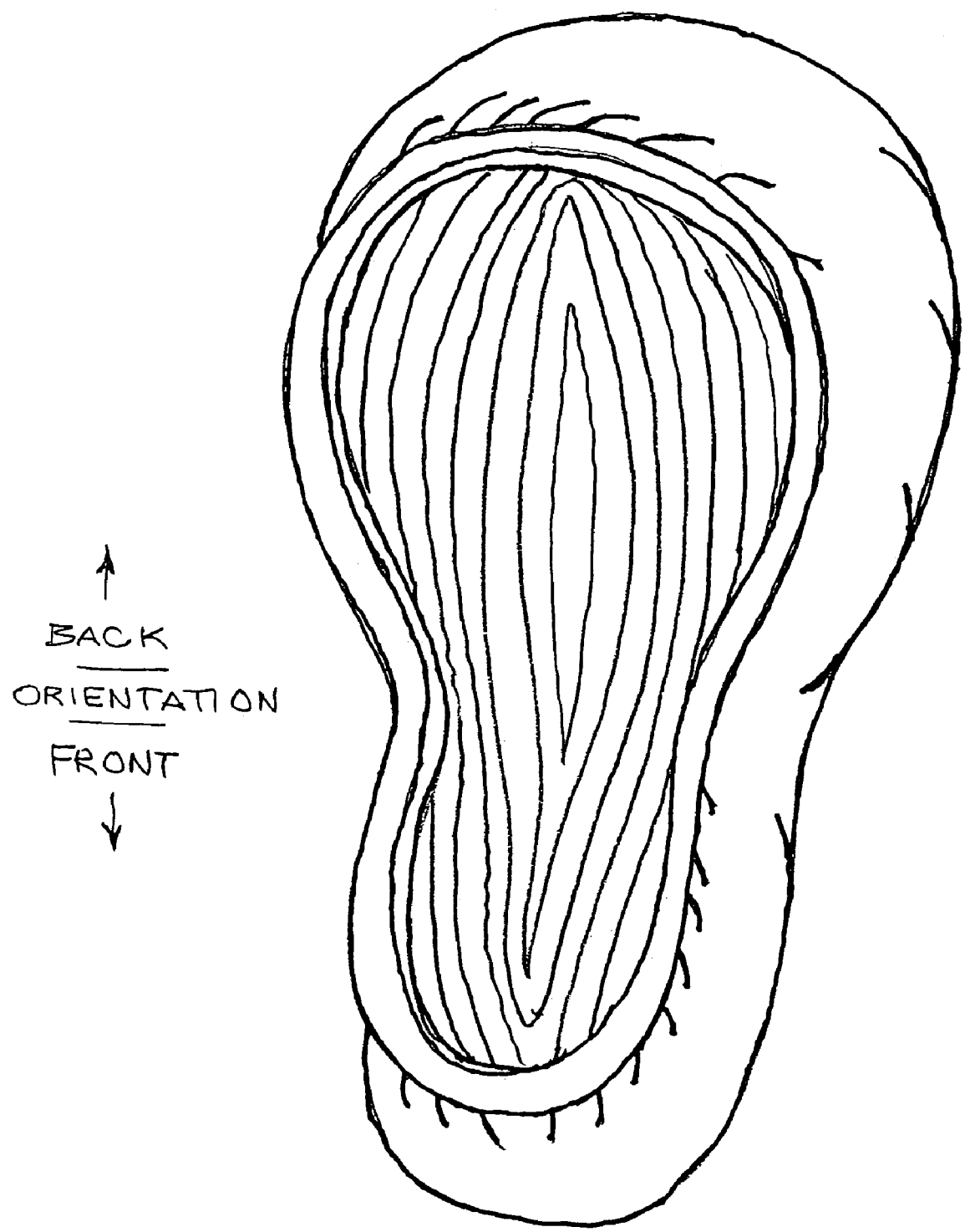
FIG. 16 is a perspective view of an alternative shape for the present invention.

Although the present invention has been described as being configured to easily align with the contours of the body, a slight modification of the above design may be ergonomically preferable. FIG. 16 discloses such a modified structural shape that provides for a narrower front facing portion and a wider portion in the back. Construction of such a shape can be easily accomplished using the known manufacturing procedures that cut, shape, tuft and gather the various materials of construction of the present invention into the intended configuration. The structure shown in FIG. 16 provides both user comfort and a wider opening into the absorbent material of the present invention to insure full coverage. The narrower front section continues to provide an adequate opening for proper receipt of fluids into the absorbent material but at the same time provides a more comfortable sized product to be positioned as shown in FIG. 11 described above.

Although the present invention has been described in conjunction with certain preferred embodiments and certain specific applications, it is anticipated that those skilled in the art will discern further embodiments and applications that fall within the scope of the invention and the following appended claims.

We claim:

1. A urinary collection apparatus comprising:
   a substantially liquid-impermeable hand enclosure having a hand aperture therein, said aperture opening into a first interior space of said hand enclosure; and
   a preformed pad comprising: (a) a waterproof shell, said waterproof shell having a shell orifice defined by a rim of said waterproof shell, said shell orifice opening into a shell receptacle space; (b) a liquid reception panel enclosed substantially within said shell receptacle space; and (c) an absorbent material situated within said shell receptacle space and secured in substantial juxtaposition with said liquid reception panel;
   said pad being affixed to an outer surface of said hand enclosure.

2. The urinary collection apparatus of claim 1 wherein said hand enclosure is sized and shaped for, upon inverting thereof, the formation of a second interior space defined by said outer surface and sized for reception of said pad fully within said second interior space.

3. The urinary collection apparatus of claim 1 wherein said rim of said pad is pre-contoured to conform to paraurethral physiology of a human female.

4. The urinary collection apparatus of claim 2 wherein said rim of said pad is pre-contoured to conform to paraurethral physiology of a human female.

5. The urinary collection apparatus of claim 1, wherein the shape of said pad is concave.

6. The urinary collection apparatus of claim 1, wherein the shape of said pad is ovoid.

7. The urinary collection apparatus of claim 1, wherein said absorbent material comprises hydrophilic gel.

8. The urinary collection apparatus of claim 1, wherein said absorbent material comprises a super-absorbent polymer.

9. The urinary collection apparatus of claim 8, wherein said hand enclosure is invertible and closeable about said pad, and wherein said pad has an ovoid, concave shape configured for collecting a urinary discharge.

* * * * *

UNITED STATES PATENT AND TRADEMARK OFFICE
CERTIFICATE OF CORRECTION

| | | |
|---|---|---|
| PATENT NO. | : 7,171,699 B2 | Page 1 of 1 |
| APPLICATION NO. | : 10/761813 | |
| DATED | : February 6, 2007 | |
| INVENTOR(S) | : Theresa Ernest and Kimberly L. Tomes | |

It is certified that error appears in the above-identified patent and that said Letters Patent is hereby corrected as shown below:

Please delete the paragraph that begins at col. 4, line 48 and continues to col. 4, line 59, which reads "Continuing, Fig. 2 illustrates . . . in the art."

Signed and Sealed this

First Day of May, 2007

JON W. DUDAS
*Director of the United States Patent and Trademark Office*